(12) United States Patent
Karim et al.

(10) Patent No.: US 9,416,067 B2
(45) Date of Patent: Aug. 16, 2016

(54) CATALYST USEFUL IN FISHER-TROPSCH SYNTHESIS

(75) Inventors: Khalid Karim, Riyadh (SA); Saleh A. Al-Sayari, Sharurah (SA)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

(21) Appl. No.: 13/995,646

(22) PCT Filed: Dec. 15, 2011

(86) PCT No.: PCT/EP2011/006374
§ 371 (c)(1),
(2), (4) Date: Jun. 19, 2013

(87) PCT Pub. No.: WO2012/084160
PCT Pub. Date: Jun. 28, 2012

(65) Prior Publication Data
US 2013/0274355 A1   Oct. 17, 2013

(30) Foreign Application Priority Data
Dec. 22, 2010 (EP) .................................... 10015923

(51) Int. Cl.
| B01J 27/187 | (2006.01) |
| C07C 1/04 | (2006.01) |
| B01J 23/889 | (2006.01) |
| B01J 37/03 | (2006.01) |
| B01J 37/16 | (2006.01) |
| C10G 2/00 | (2006.01) |

(52) U.S. Cl.
CPC ........... *C07C 1/0435* (2013.01); *B01J 23/8892* (2013.01); *B01J 27/187* (2013.01); *B01J 37/031* (2013.01); *B01J 37/16* (2013.01); *C10G 2/33* (2013.01); *C10G 2400/30* (2013.01)

(58) Field of Classification Search
None
See application file for complete search history.

(56) References Cited

U.S. PATENT DOCUMENTS

| 3,932,552 | A | 1/1976 | Starks ............................ 518/715 |
| 4,131,568 | A | 12/1978 | Bartish ............................ 502/74 |
| 4,177,203 | A | 12/1979 | Kolbel et al. | |
| 4,451,579 | A | 5/1984 | Lemanski ...................... 502/306 |
| 5,248,701 | A | 9/1993 | Soled et al. | |
| 5,958,985 | A | 9/1999 | Geerlings et al. | |
| 5,981,608 | A | 11/1999 | Geerlings ...................... 518/715 |
| 5,990,369 | A | 11/1999 | Barger ........................... 585/640 |
| 6,586,649 | B1 | 7/2003 | Botha ............................ 585/646 |
| 7,253,136 | B2 | 8/2007 | Mauldin ........................ 502/327 |
| 7,365,040 | B2 | 4/2008 | Van Berge .................... 502/260 |
| 7,375,055 | B2 | 5/2008 | Van Berge .................... 502/332 |
| 8,153,851 | B2 | 4/2012 | Gartside ........................ 585/324 |
| 2001/0006984 | A1* | 7/2001 | Lapidus et al. ............... 518/709 |
| 2002/0010221 | A1 | 1/2002 | Ionkina et al. | |
| 2003/0027874 | A1* | 2/2003 | Herron et al. ................. 518/713 |
| 2008/0033218 | A1 | 2/2008 | Lattner ........................ 568/897 |
| 2008/0262114 | A1 | 10/2008 | Reynhout | |
| 2010/0069589 | A1 | 3/2010 | Bradin | |
| 2012/0083539 | A1 | 4/2012 | Fu et al. | |
| 2012/0115967 | A1 | 5/2012 | Bezemer et al. | |
| 2014/0128486 | A1 | 5/2014 | Karim | |

FOREIGN PATENT DOCUMENTS

| CN | 201180065826 | 12/2011 |
| CN | 102500425 A | 6/2012 |
| CN | 2013800320200 | 6/2013 |
| CN | 2013800320215 | 6/2013 |
| EA | 201300736 | 12/2011 |
| EA | 201590086 | 6/2013 |
| EA | 201590105 | 6/2013 |
| EP | 1970361 | 9/2008 |
| EP | 10015923.5 | 12/2010 |
| EP | 11802287.0 | 12/2011 |
| EP | 2422876 | 2/2012 |
| EP | 12004731.1 | 6/2012 |
| EP | 13731348.2 | 6/2013 |
| EP | 13734700.1 | 6/2013 |
| GC | GCC/P/2011/20076 | 12/2011 |
| GC | 2013-24762 | 6/2013 |
| GC | 2013-24763 | 6/2013 |
| IN | 6320/DELNP/2013 | 12/2011 |
| JP | S 59179154 A | 10/1984 |
| JP | 2007-512328 A | 5/2007 |
| JP | 2013-545093 | 12/2011 |
| TH | 1301003512 | 12/2011 |
| WO | 0176736 A1 | 10/2001 |
| WO | 03041860 A2 | 5/2003 |
| WO | 03076074 A1 | 9/2003 |

(Continued)

OTHER PUBLICATIONS

Colley et al.; "Carbon Monoxide Hydrogenation Using Colbalt Manganese Oxide Catalysts: Initial Catalyst Optimization Studies"; Ind. Eng. Chem. Res.; vol. 27; 1988; pp. 1339-1344.

Commereuc et al.; "Catalytic Synthesis of Low Molecular Weight Olefins from CO and H2 with Fe(CO)5, Fe3(CO) 12, and [HFe3(CO)11)-Supported on Inorganic Oxides"; J.C.S. Chem. Comm.; 1980; pp. 154-155.

Dry; "Chemical Concepts Used for Engineering Purposes"; Studies in Surface Science and Catalysis; vol. 152; 2004; pp. 196-257.

(Continued)

*Primary Examiner* — Colin W Slifka
(74) *Attorney, Agent, or Firm* — Ballard Spahr LLP

(57) ABSTRACT

The present invention relates to a catalyst composition comprising cobalt manganese oxide which is modified with lanthanum and/or phosphorus and optionally one or more basic elements selected from the group consisting of alkali metal, alkaline earth metal and transition metal. Furthermore, a method for preparing said catalyst composition and a process for producing aliphatic and aromatic hydrocarbons by Fischer-Tropsch synthesis using said catalyst composition is provided.

17 Claims, No Drawings

(56) References Cited

FOREIGN PATENT DOCUMENTS

| WO | WO-2005-054163 A1 | 6/2005 |
|----|-------------------|--------|
| WO | PCT/EP2011/006374 | 12/2011 |
| WO | WO 2012/084160 | 6/2012 |
| WO | PCT/EP2013/063307 | 6/2013 |
| WO | PCT/EP2013/063311 | 6/2013 |
| WO | WO 2014/001350 | 3/2014 |
| WO | WO 2014/001354 | 3/2014 |

OTHER PUBLICATIONS

Extended European Search Report; European Application No. 10015923.5; Date of Mailing: Apr. 18, 2011; 6 Pages.
Keyser et al.; "Fischer-Tropsch Studies with Cobalt-Manganese Oxide Catalysts: Synthesis Performance in a Fixed Bed Reactor"; Applied Catalysis A: General; vol. 171; 1998; pp. 99-107.
Mirzaei et al.; "Fischer-Tropsch Synthesis Over Iron Manganese Catalysts: Effect of Preparation and Operating Conditions on Catalyst Performance" Advances in Physical Chemistry; vol. 2009; Article ID: 151489; 12 Pages.
Okuhara et al.; "Synthesis of Light Olefins from CO and H2 Over Highly Dispersed Ru/K-Al2O3 Derived from Ru3 (CO)12"; J.C.S. Chem. Comm.; 1981; pp. 1114-1115.
International Search Report; International Application No. PCT/EP2011/006374; International Filing Date: Dec. 15, 2011; Date of Mailing: Jan. 31, 2012; 4 Pages.
Van Der Riet et al.; "Selective Formation of C3 Hydrocarbons from Co+H2 Using Colbalt-Manganese Oxide Catalysts"; J. Chem. Soc., Chem. Commun.; 1986; pp. 798-799.
Liu Xijing et al., Effect of isomorphic substitution of lanthanum on mesoporous silica as support for Co Fisher-Tropsch synthesis catalysts, Journal of Guizhou University (Natural Science), vol. 27, No. 3, pp. 25-27 (2010).
First Office Action issued May 29, 2014 from the CCPIT Patent and Trademark Law Office for Chinese Application 201180065826, filed Dec. 15, 2011 (Applicant: Saudi Basic Indus. Corp. // 1st Named Inventor: Karim) (14 pages).
International Search Report and Written Opinion mailed on Oct. 2, 2013 for Intl. Pat. App. No. PCT/EP2013/063307 filed Jun. 25, 2013 and published as WO 2014/001350 (Applicant: Saudi Basic Indus. Corp. // 1st Named Inventor: Karim) (10 pages).
Extended European Search Report issued on Aug. 3, 2012 for European Pat. App. No. 12004731.1 filed Jun. 25, 2013 (Applicant: Saudi Basic Indus. Corp. // 1st Named Inventor: Karim) (8 pages).
International Search Report and Written Opinion mailed on Oct. 10, 2013 for Intl. Pat. App. No. PCT/EP2013/063311 filed Jun. 25, 2013 and published as WO 2014/001354 on Jan. 3, 2014 (Applicant: Saudi Basic Indus. Corp. // 1st Named Inventor: Karim) (9 pages).
U.S. Appl. No. 14/409,017, filed Jun. 25, 2013, Khalid Karim (Saudi Basic Indus. Corp.).
Notice of Allowance issued on Apr. 14, 2016 for U.S. Appl. No. 14/005,973, filed Sep. 18, 2013 and published as US-2014-0128486-A1 on May 8, 2014 (Applicant—Saudi Basic Industries Corporation) (8 pages).

* cited by examiner

CATALYST USEFUL IN FISHER-TROPSCH SYNTHESIS

CROSS REFERENCE TO RELATED APPLICATIONS

This application is a 371 of International Application No. PCT/EP2011/006374, filed Dec. 15, 2011, which claims priority to European Application No. 10015923.5, filed Dec. 22, 2010, both of which are hereby incorporated by reference in its entirety.

The present invention relates to a catalyst composition comprising cobalt manganese oxide which is modified with lanthanum and/or phosphorus and optionally one or more basic elements selected from the group consisting of alkali metal, alkaline earth metal and transition metal. Furthermore, a method for preparing said catalyst composition and a process for producing aliphatic and aromatic hydrocarbons using said catalyst composition is provided.

Gaseous mixtures comprising hydrogen ($H_2$) and carbon monoxide (CO) can be converted into a hydrocarbon product stream by a catalystic process known as Fischer-Tropsch synthesis (F-T synthesis). The most common catalysts useful in F-T synthesis ("F-T catalysts") are based on Fe and/or Co, although Ni- and Ru-based catalysts have also been described (see e.g. U.S. Pat. No. 4,177,203; Commereuc (1980) J. Chem. Soc., Chem. Commun 154-155; Okuhara (1981) J. Chem. Soc., Chem. Commun 1114-1115). Generally, Ni-based catalysts are relatively more selective for producing methane whereas Co-, Fe- and Ru-based catalysts are more selective for hydrocarbons having at least two carbon atoms (C2+ hydrocarbons). Moreover, the selectivity for C2+ hydrocarbons can be increased by decreasing the $H_2$:CO ratio, decreasing the reaction temperature and decreasing the reactor pressure.

It has been previously described that unsupported cobalt-manganese oxide catalysts can be used as an F-T catalyst having an improved selectivity for C3 hydrocarbons and a suppressed $CH_4$ selectivity (see Van der Riet (1986) J. Chem. Soc. Chem. Commun 798-799 and Keyser (1998) Applied Catalysis 171:99-107). The unsupported cobalt-manganese oxide composition suitable for use as F-T catalyst was produced by a process comprising the steps of co-precipitating cobalt and manganese oxides from cobalt- and manganese-comprising solution, calcining the precipitate to form a calcined catalyst precursor and reducing the calcined catalyst precursor to obtain the cobalt-manganese oxide catalyst composition (see Colley (1988) Ind. Eng. Chem. Res. 27:1339-1344). It was found that the catalyst precursor comprised the mixed spinels $Co_2MnO_4$ and $Co_2Mn_2O_4$. Reduction of the catalyst precursor resulted in an unsupported catalyst composition comprising metallic Co, MnO and a certain amount of mixed spinels $Co_2MnO_4$ and $Co_2Mn_2O_4$.

A major drawback of conventional unsupported cobalt-manganese oxide F-T catalysts is their relatively low activity resulting in a relatively low syngas conversion rate.

It was an object of the present invention to provide an improved Fischer-Tropsch catalyst (F-T catalyst) having superior catalyst activity while maintaining high hydrocarbon selectivity and low carbon dioxide ($CO_2$) and methane ($CH_4$) selectivity.

The solution to the above problem is achieved by providing the embodiments as described herein below and as characterized in the claims. Accordingly, the present invention provides a catalyst composition comprising cobalt; manganese; and at least one element selected from the group of lanthanum and phosphorus, wherein the relative molar ratios of the elements comprised in said composition are represented by the formula $$CoMn_aLa_bP_cM_dO_x$$

wherein:
M is one or more elements selected from the group consisting of alkali metal, alkaline earth metal and transition metal;
a is about 0.8-1.2;
b and/or c is >0— about 0.005;
d is 0— about 0.005; and
x is a number determined by the valence requirements of the other elements present.

In the context of the present invention, it was surprisingly found that the catalyst activity of a conventional cobalt manganese oxide FT-catalyst can be significantly increased when said conventional catalyst is modified with La and/or P and optionally one or more elements selected from the group consisting of alkali metal, alkaline earth metal and transition metal. Furthermore, it was found that the catalyst of the present invention has a decreased selectivity for $CO_2$ and $CH_4$ which are unwanted side products of F-T synthesis. Hence, the catalyst provided by the present invention is particularly suitable for converting a syngas mixture into a hydrocarbon comprising product stream.

The present invention accordingly relates to a lanthanum and/or phosphorus-modified unsupported cobalt manganese oxide catalyst which, after calcination and reduction, comprises a mixture comprising metallic Co, MnO and the mixed spinels $Co_2MnO_4$ and $Co_2Mn_2O_4$. In addition thereto, the unsupported cobalt manganese oxide catalyst of the present invention may be modified with one or more elements selected from the group consisting of alkali metal, alkaline earth metal and transition metal.

The molar ratio of Co:Mn is about 1:0.8-1.2 (depicted as: $CoMn_a$ wherein a is 0.8-1.2). This means that the molar ratio of Co:Mn is between about 1:0.8: and about 1:1.2. More preferably, the molar ratio of Co:Mn is about 1:0.9-1.1. Most preferably, the molar ratio of Co:Mn is about 1:1. The molar ratio of Co:Mn appears to be very important to obtain a catalyst composition having a high light olefin selectivity and a low methane selectivity. The relative ratio of cobalt and manganese has a strong effect on selectivity of the catalyst for hydrocarbons. When the Co:Mo ratio is too high, the hydrogenation activity of the catalyst is increased leading to an increased methane selectivity.

The catalyst composition of the present invention comprises at least one element selected from the group consisting of lanthanum and phosphorus. In one embodiment, accordingly, the catalyst comprises lanthanum but does not comprise phosphorus. In one embodiment, the catalyst comprises phosphorus but does not comprise lanthanum. In one preferred embodiment, the catalyst comprises both lanthanum and phosphorus.

The amount of lanthanum and/or phosphorus present in the catalyst composition is determined by the molar ratio of the cobalt in relation to said lanthanum and/or phosphorus in the catalyst composition. The molar ratio of Co:"at least one element selected from the group consisting of La and P" ("Co:La and/or P") is 1: >0—0 about 0.005 (depicted as $CoLa_bP_c$ wherein b and/or c is >0— about 0.005). The term ">0" means that said element must be present in the catalyst composition.

In case the catalyst composition comprises La, the molar ratio Co:La is up to 1: about 0.005 (1: about 5E-3; also depicted as: $CoLa_b$ wherein b is >0— about 0.005) and preferably up to 1: about 1E-3. Preferably, the molar ratio of Co:La is at least 1: about 1E-6 in case the catalyst composition comprises La, more preferably at least 1: about 1E-5, and most preferably at least 1: about 5E-5.

In case the catalyst composition comprises P, the molar ratio Co:P is up to 1: about 0.005 (1: about 5E-3; also depicted as: $CoP_c$ wherein c is >0— about 0.005) and preferably up to 1: about 1E-3. Preferably, the molar ratio of Co:P is at least 1: about 1E-6 in case the catalyst composition comprises P, more preferably at least 1: about 1E-5, and most preferably at least 1: about 5E-5.

The catalyst composition of the present invention further may comprise one or more additional elements selected from the group consisting of alkali metal element, alkaline earth metal element and transition metal element (depicted herein as "M"). In the context of the present invention, it was found that $CO_2$ formation and the therewith associated coke deposition by the Boudouard reaction can be suppressed when the catalyst composition further comprises one or more basic elements selected from the group consisting of alkali metal elements, alkaline earth metal elements and transition metal elements. As used herein, the term "basic element" relates to an element that forms a "Lewis base" (i.e. an element that is able to provide a pair of electrons and thus capable of coordination to a Lewis acid, thereby producing a Lewis adduct) and/or a "Brønsted base" (i.e. an element capable of accepting a proton from a acid or the corresponding chemical species) in the catalyst composition.

Preferably, the one or more alkali metals that may be comprised in the catalyst composition are selected from the group consisting of sodium (Na), potassium (K), rubidium (Rb) and caesium (Cs), more preferably selected from the group consisting of sodium (Na), potassium (K) and caesium (Cs), and most preferably is potassium (K). The one or more alkaline earth metals that may be comprised in the catalyst composition are preferably selected from the group consisting of magnesium (Mg), calcium (Ca), strontium (Sr) and barium (Ba), and more preferably selected from the group consisting of magnesium (Mg) and calcium (Ca). The one or more transition metal elements that may be comprised in the catalyst composition of the present invention are preferably selected from "Group 4 of the Periodic Table" and more preferably selected from the group consisting of titanium (Ti) and zirconium (Zr).

The amount of alkali metal, alkaline earth metal and/or transition metal elements ("M") that may be comprised in the catalyst composition of the present invention is determined by the molar ratio in relation to the cobalt present in the catalyst composition. In case the catalyst composition comprises M, the molar ratio Co:M is up to 1: about 0.005 (1: about 5E-3; also depicted as: $CoM_d$ wherein d is >0— about 0.005) and preferably up to 1: about 1E-3. Preferably, the molar ratio of Co:M is at least 1: about 1E-6 in case the catalyst composition comprises M, more preferably at least 1: about 1E-5, and most preferably at least 1: about 5E-5.

In this respect, it should be noted that the catalyst of the present invention is a mixed oxide catalyst and not a catalyst wherein the active elements are deposited on a catalyst support. The unsupported catalyst of the present invention is fundamentally different than F-T catalysts wherein Co and Mn are deposited on a (metal) oxide catalyst support. Nevertheless, the catalyst composition may further comprise a (metal) oxide, e.g. as a binder or a diluent.

Accordingly, the catalyst composition of the present invention may further comprise a binder which preferably is selected from the group consisting of silica, alumina, titania, zirconium, carbon and zeolite. The zeolite may be a mesoporous zeolite or a microporous zeolite.

In a further embodiment, the present invention relates to a method for preparing the catalyst composition as described herein, wherein said method comprises the steps:
  (a) preparing a solution of cobalt- and manganese-comprising salts to form a cobalt-manganese-solution;
  (b) admixing an alkaline solution to the cobalt-manganese-solution to form a precipitate;
  (c) admixing a solution of a lanthanum-comprising salt; and/or a solution of a phosphorus-comprising salt; and preferably a solution of a salt comprising one or more elements selected from the group consisting of alkali metal elements, alkaline earth metal elements and transition metal elements to the solution comprising the precipitate to form a modified precipitate;
  (d) separating the modified precipitate from the liquid, washing and drying the modified precipitate to form a dried precipitate;
  (e) calcining the dried precipitate in air to form a calcined catalyst precursor; and
  (f) contacting the calcined catalyst precursor with a reducing agent.

Preferably, the method for preparing the catalyst composition of the invention comprises the steps (a)-(f) in the herein above described order.

In the cobalt-manganese-solution preparation step (a) as described herein, a solution comprising soluble cobalt- and manganese-comprising salts is prepared. The solvent and the obtained solution may be heated to facilitate dissolving of the cobalt- and manganese-comprising salts. Preferably, the solvent and the obtained solution is heated to at least about 60° C. and up to about 95° C. (about 60-95° C.), most preferably to about 80° C.

In the present method for preparing the catalyst composition, the solution may be made in any suitable solvent. Suitable solvents are all compounds in which the chosen salts are soluble and which are easy to remove again in the separation step as defined herein. Aqueous solutions, however, are preferred. Most preferably, the solvent is water ($H_2O$).

In the precipitate forming step (b) as described herein, a precipitate is formed by converting the soluble cobalt- and manganese-comprising salts into insoluble compounds by admixing an alkaline solution, preferably under constant agitation. Preferably, the precipitate is formed by admixing a suitable amount of ammonium hydroxide and/or sodium carbonate solution, preferably ammonium hydroxide solution, to a cobalt-manganese-solution. The amount of alkaline compound present in the alkaline solution is selected so that it is at least sufficient for the stoichiometric reaction with the soluble cobalt- and manganese-comprising salts present. Preferably, the amount of alkaline compound present in the alkaline solution is 1-10 times the stoichiometric required amount. Preferably, the ammonium hydroxide and/or sodium carbonate solution is heated to the same temperature as the cobalt-manganese-solution. The temperature of the mixture may be kept constant until the precipitate is formed under constant agitation.

In the modified precipitate forming step (c) as described herein, a solution of a lanthanum-comprising salt; and/or a solution of a phosphorus-comprising salt; and preferably a solution of a salt comprising one or more elements selected from the group consisting of the alkali metal elements, the alkaline earth metal elements and the transition metal elements is admixed to the solution comprising the precipitate, preferably under continuous agitation, to form a modified precipitate. The solution of a salt comprising one or more elements selected from the group consisting of the alkali metal elements, the alkaline earth metal elements and the transition metal elements is preferably added at the same time or after adding the solution of a lanthanum-comprising salt; and/or a solution of a phosphorus-comprising salt. Most preferably, the solution of a salt comprising one or more elements selected from the group consisting of the alkali metal elements, the alkaline earth metal elements and the transition metal elements is added after adding the solution of a lanthanum-comprising salt; and/or a solution of a phosphorus-comprising salt. The solutions used in the modified precipitate forming step may be made in any suitable solvent. Aqueous solutions, however, are preferred. Most preferably, the solvent is water ($H_2O$).

In the precipitate separation step (d) as described herein, the modified precipitate (i.e. the solid phase of the mixture that is formed after completing the modified precipitate forming step (c)) is separated from the liquid (i.e. the liquid phase of the mixture that is formed after completing the modified precipitate forming step (c)) using any conventional method which allows the separation of a precipitate from a solvent. Suitable methods include, but are not limited to, filtering, decanting and centrifugation. Subsequently the obtained precipitate is washed using the solvent in which the solutions were made, preferably with water, most preferably with distilled water. The modified precipitate is then dried, preferably at about 110-120° C. for about 4-16 hours to form a dried precipitate.

In the calcining step (e) as described herein, the dried precipitate is calcined in air to form a calcined catalyst precursor. Preferably, the dried precipitate is calcined at about 500-600° C. for about 4-24 hours. The calcined but unreduced catalyst mainly comprises the spinel $Co_2MnO_4$.

After calcination, the calcined catalyst precursor is preferably formed into pellets using any conventional method. Said pellets may subsequently be sieved to obtain regularly sized particles. Said particles may be sized between about 0.65-0.85 mm.

In the reducing step (f) as described herein, the calcined catalyst precursor is contacted with a reducing agent. This is to partially reduce the comprised Co to its metallic state and results in the formation of cobalt manganese oxide comprising catalyst as defined herein. In addition thereto, the catalyst composition comprises metallic Co supported on MnO at the end of the reducing step. Hence, the MnO is not reduced completely into metallic Mn. Accordingly, the catalyst composition of the present invention, inter alia comprising metallic cobalt, MnO and mixed spinels having the formula $Co_2MnO_4$ and $Co_2Mn_2O_2$, is obtainable by the herein described method for preparing a catalyst composition after the "reducing step" is finished.

Accordingly, the reducing step is very important for the method for preparing a catalyst composition of the present invention. When the reducing step is performed too mild, an insufficient amount of Co is reduced to its metallic state. When the reducing step is performed too harsh, the catalyst composition comprises an insufficient amount of "cobalt manganese oxide" and/or MnO. The skilled person can easily determine that the catalyst obtained catalyst composition comprises metallic cobalt, MnO and cobalt manganese oxide by using standard analytical techniques, including X-ray diffraction.

Any suitable reducing agent may be used in the reducing step of this invention. Preferably, the reducing step is performed using a reducing agent in the gas phase. The preferred reducing agent is selected from the group consisting of hydrogen ($H_2$) and carbon monoxide (CO). The reduction can be carried out at ambient temperature or at elevated temperature. Preferably, the reduction is carried out at a temperature of at least about 300° C., more preferably of at least about 350° C. and up to about 500° C., more preferably up to about 450° C. Preferably, calcined catalyst precursor is contacted with a reducing agent for at least about 14 hrs, more preferably for at least about 16 hrs and up to about 24 hrs, more preferably up to about 20 hrs.

Preferably, the reducing step is performed "in situ". The term "in situ" is well known in the field of chemical engineering and refers to industrial plant operations or procedures that are performed in place. For example, aged catalysts in industrial reactors may be regenerated in place (in situ) without being removed from the reactors; see e.g. WO 03/041860 and WO 03/076074. In the context of the present invention, accordingly, a catalyst composition that is reduced in situ refers to a catalyst composition wherein the reducing step is performed in place, i.e. in the same enclosure that is later present in the process installation in which the catalysed process takes place. In one embodiment, the reducing step as defined herein is performed while the "calcined catalyst precursor" is already present in the catalyst enclosure that is situated in the process installation wherein the catalyst composition is to be employed. In a further embodiment, the reducing step as defined herein is performed while the "calcined catalyst precursor" is already present in the catalyst enclosure which can be directly placed into said process installation.

In a further embodiment of the present invention a catalyst composition obtainable by the herein above described method for preparing a catalyst composition is provided. Accordingly, the present invention relates to a catalyst composition obtainable by the method comprising the steps:
 (a) preparing a solution of cobalt- and manganese-comprising salts to form a cobalt-manganese-solution;
 (b) admixing to the cobalt-manganese-solution to form a precipitate;
 (c) admixing a solution of a lanthanum-comprising salt; and/or a solution of a phosphorus-comprising salt; and preferably a solution of a salt comprising one or more elements selected from the group consisting of alkali metal elements, alkaline earth metal elements and transition metal elements to the solution comprising the precipitate to form a modified precipitate;
 (d) separating the modified precipitate from the liquid, washing and drying the modified precipitate to form a dried precipitate;
 (e) calcining the dried precipitate in air to form a calcined catalyst precursor; and
 (f) contacting the calcined catalyst precursor with a reducing agent.

In a further embodiment, the present invention relates to a process for producing a product stream comprising a mixture of aliphatic and aromatic hydrocarbons comprising contacting the catalyst composition as described herein with a gaseous mixture comprising hydrogen and carbon monoxide (syngas mixture). The product stream comprising a mixture of aliphatic and aromatic hydrocarbons is preferably produced by Fischer-Tropsch synthesis.

The terms "aliphatic hydrocarbons" and "aromatic hydrocarbons" are very well known in the art. Accordingly, an "aliphatic hydrocarbons" relates to acyclic or cyclic, saturated or unsaturated hydrocarbon compounds that are not aromatic hydrocarbons. The term "aromatic hydrocarbons" relates to cyclically conjugated hydrocarbons with a stability (due to delocalization) that is significantly greater than that of a hypothetical localized structure (e.g. Kekulé structure). The most common method for determining aromaticity of a given hydrocarbon is the observation of diatropicity in the $^1$H NMR spectrum.

In the context of the present invention, it was surprisingly found that substantially no waxes are produced in the process for Fischer-Tropsch synthesis of the present invention. Moreover, it was found that the selectivity for lower hydrocarbons having between 2 and 5 carbon atoms (C2-C5 HC) and aromatic hydrocarbons is increased.

In the process of the present invention, the catalyst composition is preferably comprised in a fixed bed reactor or a fluidized bed reactor.

Preferably, the syngas mixture has a hydrogen ($H_2$) to carbon monoxide (CO) molar ratio of about 1-4 (i.e. $H_2$: CO is 1:about 1-4). The term "syngas mixture" as used herein relates to a gaseous mixture substantially consisting of hydrogen ($H_2$) to carbon monoxide (CO). The syngas mixture, which is used as a feed stream to the present process for producing aliphatic and aromatic hydrocarbons, may comprise up to 10 mol-% of other components such as $CO_2$ and lower hydrocarbons (lower HC). Said other components may be side-products or unconverted products obtained in the process used for producing the syngas mixture. Preferably, the syngas mixture comprises substantially no molecular oxygen ($O_2$). As used herein, the term "syngas mixture comprising substantially no $O_2$" relates to a syngas mixture which comprises such a low amount of $O_2$ so that the comprised $O_2$ does not interfere with the Fischer-Tropsch synthesis reaction. Preferably, the syngas mixture comprises not more than 1 mol-% $O_2$, more preferably not more than 0.5 mol-% $O_2$ and most preferably not more than 0.4 mol-% $O_2$.

The process conditions useful in the process of the present invention can be easily determined by the person skilled in the art; see Dry (2004) Stud. Surf. Sci. Catal 152:197-230 in "Fischer-Tropsch technology" eds. Steynberg and Dry. Accordingly, the Fischer-Tropsch synthesis is performed at a reaction temperature of of about 150-350° C., a space velocity of about 400-5000 h$^{-1}$, preferably of about 2000 h$^{-1}$ and a pressure of between atmospheric and about 5 MPa. The catalyst may be stabilized for about 80-100 hours at about 150-350° C. before actual use.

In this respect, it should be noted that the reaction conditions have a marked effect on the catalytic performance. It has been reported that selectivity on a carbon basis is essentially a function of the probability of chain growth, α; see Dry (2004) loc. cit. Control of the product selectivity is to a large extent determined by the factors that influence the value of α. The main factors are the temperature of the reaction, the gas composition and more specifically the partial pressures of the various gases in contact with catalyst inside the reactor. Overall, by manipulating these factors a high degree of flexibility can be obtained regarding the type of product and the carbon range. An increase in FT-synthesis operating temperature shifts the selectivity profile to lower carbon number products. Desorption of growing surface species is one of the main chain termination steps and since desorption is an endothermic process so a higher temperature should increase the rate of desorption which will result in a shift to lower molecular mass products. Similarly, the higher the CO partial pressure the more is the catalyst surface covered by adsorbed monomers. The lower the coverage by partially hydrogenated CO monomers the higher the probability of chain growth is expected to be; see also Mirzaei et al., Adv. Phys. Chem., 2009,1-12. Accordingly, the two key steps leading to chain termination are desorption of the chains yielding alkenes and hydrogenation of the chains to yield alkanes.

In a further embodiment, the present invention relates to a process for producing a product stream comprising a mixture of aliphatic and aromatic hydrocarbons comprising the method for preparing the catalyst composition as described herein and contacting the obtained catalyst composition with a syngas mixture.

In the present invention, the product stream comprising a mixture of aliphatic and aromatic hydrocarbons is preferably produced by Fischer-Tropsch synthesis.

Accordingly, the present invention provides a process for producing a product stream comprising a mixture of aliphatic and aromatic hydrocarbons, preferably by Fischer-Tropsch synthesis, comprising:

(a) preparing a solution of cobalt- and manganese-comprising salts to form a heated cobalt- manganese-solution;

(b) admixing ammonium hydroxide or sodium carbonate solution to the cobalt-manganese-solution to form a precipitate;

(c) admixing a solution of a lanthanum-comprising salt; and/or a solution of a phosphorus-comprising salt; and preferably a solution of a salt comprising one or more elements selected from the group consisting of alkali metal elements, alkaline earth metal elements and transition metal elements to the solution comprising the precipitate to form a modified precipitate;

(d) separating the modified precipitate from the liquid, washing and drying the modified precipitate to form a dried precipitate;

(e) calcining the dried precipitate in air to form a calcined catalyst precursor;

(f) contacting the calcined catalyst precursor with a reducing agent to produce a catalyst composition; and (g) contacting the obtained catalyst composition with a syngas mixture.

MODE(S) FOR CARRYING OUT THE INVENTION

The present invention will now be more fully described by the following non-limiting Examples.

EXAMPLE 1

Comparative

CoMnOx 100 ml of Co and Mn (1M solutions) were premixed and heated to 80° C. in a round bottom flask. Ammonium hydroxide solution (5.6 M/I) preheated at 80° C. was added to the nitrate solution, which was continuously stirred whilst the temperature was maintained at 80° C. The pH was varied from 2.80 to 8.0. The precipitates were first filtered and then washed several times with warm distilled water. The precipitates were then dried at 110° C. for 16 h to give a material denoted as the dried precipitate. This dried precipitate was then calcined in air at 500-600° C. for 24 h to produce a calcined catalyst precursor. The calcined catalyst precursor was pelleted and sieved to obtain 0.65-0.85 mm sized particles.

Calcined precursor particles (0.5 g) were loaded into a fixed-bed laboratory reactor. The catalyst precursor was subsequently reduced in situ at 400° C. for 16 h, in a hydrogen atmosphere (GHSV=600 h$^{-1}$). Temperature was reduced to room temperature and syngas was switched on for reaction. Pressure was increased to 600 KPa (6 barg) at GHSV=600 h$^{-1}$. A stabilization period of 100 h after initiation of FT synthesis was allowed before mass balance data collection. Calibrated GC was used to determine the products and mass balance. The obtained results are summarized in Table 1 provided herein below.

The provided values have been calculated as follows:

Conversion:

An indication of the activity of the catalyst was determined by the extent of conversion of the carbon monoxide or for more active catalysts by the extent of volume reduction of the reagent gases (using nitrogen as internal standard). The basic equation used was Conversion %=Moles of $CO_{in}$−moles of $CO_{out}$/moles of $CO_{in}$* 100/1

Selectivity

First of all, the varying response of the detector to each product component was converted into % v/v by, multiplying them with online calibration factors. Then these were converted into moles by taking account the flow out of internal standard, moles of feed in and time in hours. Moles of each product were converted into mole-% and selectivity-% was measured by taking carbon numbers into account.

EXAMPLE 2

CoMnLaP (Comprising 0.1 wt-% La and 0.03 wt-% P)

100 ml of Co and Mn (1 M solutions) were premixed and heated to 80° C. in a round bottom flask. Ammonium hydroxide solution (5.6 M/I) preheated at 80° C. was added to the nitrate solution, which was continuously stirred whilst the temperature was maintained at 80° C. The pH was varied from 2.80 to 8.0. Required quantity of lanthanum nitrate (0.0117 g) was dissolved in 3.4 ml of distilled water and was added slowly into the of CoMn catalyst precipitate (5 g) followed by addition of 0.0064 g of ammonium phosphate dissolved in 3.4 ml of distilled water. The resulting precipitate was mixed thoroughly to make a homogeneous mixture. Material was dried at 110° C. for 16 h-24 h and calcined at 500-600° C. for 24 h. The calcined catalyst precursor was pelleted and sieved to obtain 0.65-0.85 mm sized particles.

Calcined precursor particles (0.5 g) were loaded into a fixed-bed laboratory reactor. The catalyst was then reduced in situ and was tested under identical reaction conditions as described in Example 1 (CO/$H_2$=1/1, T=220° C., P=600 kPa (6 barg), and GHSV=600 $h^{-1}$). Data were collected as described in Example 1. The obtained results are summarized in Table 1 provided herein below.

EXAMPLE 3

CoMnP (Comprising 0.05 wt-% P)

100 ml of Co and Mn (1 M solutions) were premixed and heated to 80° C. in a round bottom flask. Ammonium hydroxide solution (5.6 M/l) preheated at 80° C. was added to the nitrate solution, which was continuously stirred whilst the temperature was maintained at 800° C. The pH was varied from 2.80 to 8.0. Required quantity of ammonium phosphate (0.0107 g) dissolved in 3.4 ml of distilled water was added slowly into the of CoMn catalyst precipitate (5 g). The resulting precipitate was mixed thoroughly to make a homogeneous mixture. Material was dried at 110° C. for 16 h-24 h and calcined at 500-600° C. for 24 h. The calcined catalyst precursor was pelleted and sieved to obtain 0.65-0.85 mm sized particles.

Calcined precursor particles (0.5 g) were loaded into a fixed-bed laboratory reactor. The catalyst was then reduced in situ and was tested under identical reaction conditions as described in Example 1 (CO/$H_2$=1/1, T=220° C., P=600 kPa (6 barg), and GHSV=600 $h^{-1}$). Data were collected as described in Example 1. The obtained results are summarized in Table 1 provided herein below.

EXAMPLE 4

CoMnPK (Comprising 0.05 wt-% P and 0.15 wt-% K)

100 ml of Co and Mn (1 M solutions) were premixed and heated to 80° C. in a round bottom flask. Ammonium hydroxide solution (5.6 M/I) preheated at 80° C. was added to the nitrate solution, which was continuously stirred whilst the temperature was maintained at 800° C. The pH was varied from 2.80 to 8.0. Required quantity of ammonium phosphate (0.0043 g) dissolved in 3.4 ml of distilled water was added slowly into the of CoMn catalyst precipitate (5 g). The required amount of potassium acetate (0.076 g) dissolved in 3.4 ml of distilled water was added slowly into the CoMnP catalyst precipitate (5 g). The resulting precipitate was mixed thoroughly to make a homogeneous mixture. Material was dried at 110° C. for 16 h-24 h and calcining at 500-600° C. for 24 hrs. The calcined catalyst precursor was pelleted and sieved to obtain 0.65-0.85 mm sized particles.

Calcined precursor particles (0.5 g) were loaded into a fixed-bed laboratory reactor. The catalyst was then reduced in situ and was tested under identical reaction conditions as described in Example 1 (CO/$H_2$=1/1, T=220° C., P=600 kPa (6 barg), and GHSV=600 $h^{-1}$). Data were collected as described in Example 1. The obtained results are summarized in Table 1 provided herein below.

TABLE 1

Syngas conversion to hydrocarbons

| catalyst | Example 1 (comparative) CoMnOx | Example 2 CoMnLaP | Example 3 CoMnP | Example 4 CoMnPK |
|---|---|---|---|---|
| Conversion % | 15.1 | 42.4 | 21.7 | 28.6 |
| Selectivity % | | | | |
| methane | 18.4 | 13.1 | 14.2 | 17.5 |
| ethane | 9.4 | 4.7 | 8.0 | 10.2 |
| ethylene | 1.0 | 0.9 | 0.9 | 0.7 |
| propane | 8.5 | 6.1 | 8.3 | 9.9 |
| propylene | 21.6 | 19.8 | 24.4 | 21.1 |
| n-butane | 5.4 | 4.4 | 5.1 | 5.1 |
| 1-butene | 8.8 | 10.5 | 8.8 | 6.7 |
| iso-butylene | 0.5 | 0.3 | 0.6 | 0.6 |
| cis-2-butene | 2.1 | 1.9 | 3.2 | 3.3 |
| C5-C6 HC | 14.2 | 22.0 | 13.8 | 13.1 |
| $CO_2$ | 10.2 | 6.3 | 8.0 | 8.9 |

Table 1 clearly shows that the catalyst of the present invention has a significantly increased activity when compared to a conventional cobalt manganese oxide F-T catalyst. In addition thereto, a decrease in $CO_2$ and methane formation could be observed, which are undesired side-products produced in F-T synthesis.

The invention claimed is:

1. A catalyst composition comprising:
cobalt; manganese; and at least one element selected from the group of lanthanum and phosphorus,
wherein the relative molar ratios of the elements comprised in the composition are represented by the formula $CoMn_aLa_bP_cM_dO_x$ wherein:

M is one or more elements selected from the group consisting of alkali metal, alkaline earth metal and transition metal;

a is about 0.8-1.2;

b is 0 to about 0.005;

c is greater than 0 to about 0.005;

d is 0 to about 0.005; and x is a number determined by the valence requirements of the other elements present, wherein the catalyst is unsupported.

2. The catalyst according to claim 1, wherein d is greater than 0 to about 0.005 and wherein M is selected from the group consisting of sodium (Na), potassium (K), rubidium (Rb), cesium (Cs), magnesium (Mg), calcium (Ca), strontium (Sr), barium (Ba), titanium (Ti) and zirconium (Zr).

3. The catalyst composition according to claim 2, comprising cobalt; manganese; lanthanum; phosphorus, and M, wherein: b is greater than 0 to about 0.005; c is greater than 0 to about 0.005; and d is greater than 0 to about 0.005, and wherein M is selected from the group consisting of Na, K, Rb, Cs, Mg, Ca, Sr, Ba, Ti, and Zr.

4. The catalyst composition according to claim 2, comprising cobalt; manganese; lanthanum; phosphorus, and M, wherein: b is greater than 0 to about 0.005; c is greater than 0 to about 0.005; and d is greater than 0 to about 0.005 and wherein M is selected from the group consisting of Na, K, and Cs.

5. The catalyst composition according to claim 2, comprising cobalt; manganese; lanthanum; phosphorus, and M, wherein: b is greater than 0 to about 0.005; c is greater than 0 to about 0.005; and d is greater than 0 to about 0.005, and wherein M is K.

6. The catalyst composition according to claim 2, wherein c is greater than 0 to about 0.005, and wherein M is K.

7. The catalyst composition according to claim 1, comprising cobalt; manganese; lanthanum; and phosphorus, wherein: b is greater than 0 to about 0.005; and c is greater than 0 to about 0.005.

8. The catalyst composition according to claim 1, wherein the catalyst composition further comprises a binder selected from the group consisting of silica, alumina, titania, zirconium, carbon and zeolite.

9. The catalyst composition according to claim 1, wherein the catalyst composition has a decreased selectivity for the production of $CO_2$ and $CH_4$ as compared to a comparative $CoMnO_x$ catalyst composition without the La and/or P.

10. A method for preparing the catalyst composition according to claim 1, comprising:

(a) preparing a solution of cobalt- and manganese-comprising salts to form a cobalt-manganese-solution;

(b) admixing an alkaline solution to the cobalt- manganese-solution to form a precipitate;

(c) admixing a solution of a phosphorus-comprising salt; and optionally a solution of a lanthanum-comprising salt to the solution comprising the precipitate to form a modified precipitate;

(d) separating the modified precipitate from the liquid, washing and drying the modified precipitate to form a dried precipitate;

(e) calcining the dried precipitate in air to form a calcined catalyst precursor; and (f) contacting the calcined catalyst precursor with a reducing agent.

11. The method according to claim 10, wherein the reducing agent is selected from the group consisting of hydrogen ($H_2$) and carbon monoxide (CO).

12. The process according to claim 10, wherein admixing the solution of the phosphorus-comprising salt and optionally the solution of the lanthanum-comprising salt with the precipitate further comprises admixing a solution of a salt comprising one or more elements selected from the group consisting of alkali metal elements, alkaline earth metal elements and transition metal elements.

13. A process for producing a product stream comprising: contacting the catalyst composition as defined in claim 1 with a syngas mixture to produce a mixture of aliphatic and aromatic hydrocarbons.

14. The process according to claim 13, wherein the product stream is produced by Fischer-Tropsch synthesis.

15. The process according to claim 14, wherein the Fischer-Tropsch synthesis is performed at a reaction temperature of about 150-350° C., a space velocity of about 400-5000 $h^{-1}$ and a pressure of between atmospheric and about 5 MPa.

16. The process according to claim 13, wherein the catalyst composition is in a fixed bed reactor or fluidized bed reactor.

17. The process according to claim 13, wherein the syngas mixture has a hydrogen ($H_2$) to carbon monoxide (CO) molar ratio of about 1-4.

* * * * *